(12) United States Patent
Fessmann et al.

(10) Patent No.: US 7,014,663 B2
(45) Date of Patent: Mar. 21, 2006

(54) COMPOUNDS DERIVED FROM DIAMINOPYRAZOLES SUBSTITUTED BY AN AMINOALKYL OR AMINOALKENYL RADICAL AND THEIR USE IN OXIDATION DYEING OF KERATINOUS FIBRES

(75) Inventors: Thilo Fessmann, Aulnay-sous-Bois (FR); Eric Terranova, Magagnosc (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 10/484,131

(22) PCT Filed: Jul. 9, 2002

(86) PCT No.: PCT/FR02/02396

§ 371 (c)(1),
(2), (4) Date: Aug. 16, 2004

(87) PCT Pub. No.: WO03/008385

PCT Pub. Date: Jan. 30, 2003

(65) Prior Publication Data

US 2005/0015893 A1    Jan. 27, 2005

(30) Foreign Application Priority Data

Jul. 18, 2001    (FR) .................................. 01 09623

(51) Int. Cl.
*A61K 7/13*    (2006.01)

(52) U.S. Cl. ..................... 8/405; 8/406; 8/409; 8/410; 8/411; 8/412; 8/523; 8/568; 8/570; 8/579; 548/302.7

(58) Field of Classification Search ............ 8/405, 8/406, 409, 410, 411, 412, 423, 568, 570, 8/579; 548/302.7
See application file for complete search history.

(56) References Cited

U.S. PATENT DOCUMENTS

| | | | |
|---|---|---|---|
| 5,061,289 A | 10/1991 | Clausen et al. ................. | 8/405 |
| 5,865,855 A * | 2/1999 | Doehling et al. ............... | 8/409 |
| 6,099,592 A | 8/2000 | Vidal et al. .................... | 8/409 |
| 6,660,046 B1 | 12/2003 | Terranova et al. .............. | 8/405 |

FOREIGN PATENT DOCUMENTS

| | | |
|---|---|---|
| DE | 20013156 U1 * | 10/2000 |
| EP | 0375977 | 7/1990 |
| EP | 0740931 | 11/1996 |
| WO | WO 94/08969 | 4/1994 |
| WO | WO 98/17234 | 4/1998 |
| WO | WO 98/20847 | 5/1998 |
| WO | WO 00/43367 | 7/2000 |

OTHER PUBLICATIONS

STIC Search Report dated Jan. 5, 2005.*

* cited by examiner

*Primary Examiner*—Eisa Elhilo
(74) *Attorney, Agent, or Firm*—Fulbright & Jaworski L.L.P.

(57) ABSTRACT

The invention concerns compounds derived from diaminopyrazole of formula (I), wherein: $R_1$ is a linear or branched radical selected among $C_2$, $C_3$, $C_4$ aminoalkyl radicals or $C_2$, $C_3$, $C_4$ aminoalkenyl radicals, or one of the physiologically acceptable salts thereof. The invention also concerns compositions containing said compound for dyeing keratinous fibers and the method using said compositions.

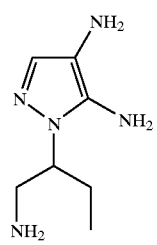

24 Claims, No Drawings

COMPOUNDS DERIVED FROM DIAMINOPYRAZOLES SUBSTITUTED BY AN AMINOALKYL OR AMINOALKENYL RADICAL AND THEIR USE IN OXIDATION DYEING OF KERATINOUS FIBRES

This application is a U.S. national phase application under 35 U.S.C. § 371 of International Application No. PCT/FR02/02396 filed 9 Jul. 2002, which claims priority to French Application No. 01/09623 filed 18 Jul. 2001, the entire disclosures of which are incorporated herein by reference.

The present invention relates to novel compounds derived from diaminopyrazole, to a composition for the oxidation dyeing of keratin fibers, and in particular of human keratin fibers such as the hair, comprising at least one compound derived from diaminopyrazole as oxidation base, and to the oxidation dyeing processes using it.

It is known practice to dye keratin fibers, and in particular human hair, with dye compositions containing oxidation dye precursors, in particular ortho- or para-phenylenediamines, ortho-aminophenols or para-aminophenols and heterocyclic compounds such as diaminopyrazole derivatives, which are generally referred to as oxidation bases. The oxidation dye precursors, or oxidation bases, are colorless or weakly colored compounds which, when combined with oxidizing products, can give rise to colored compounds and dyes by a process of oxidative condensation.

It is also known that the shades obtained with these oxidation bases can be varied by combining them with couplers or coloration modifiers, the latter being chosen in particular from aromatic meta-diamines, meta-aminophenols, meta-diphenols and certain heterocyclic compounds.

The variety of molecules used as oxidation bases and couplers makes it possible to obtain a wide range of colors.

The so-called "permanent" coloration obtained by means of these oxidation dyes must moreover satisfy a certain number of requirements. Thus, it must have no toxicological drawbacks and it must allow shades of the desired strength to be obtained and have good resistance to external agents (light, bad weather, washing, permanent-waving, perspiration and friction).

The dyes must also allow white hairs to be covered, and, lastly, they must be as unselective as possible, i.e. they must allow the smallest possible differences in coloration to be produced over the entire length of the same keratin fiber, which may indeed be differently sensitized (i.e. damaged) between its tip and its root. They must also show good chemical stability in the formulations, and must have a good toxicological profile.

Furthermore, for a certain number of applications, dyes that produce chromatic shades on the hair are desired.

Application EP 375 977 discloses 4,5-diaminopyrazole compounds of use as coloring agent in oxidation dyeing. Patent application EP 871 426 also discloses compositions comprising 4,5-diaminopyrazole derivatives substituted in the 1 position by an alkyl, mono- or polyhydroxyalkyl or mono- or polyaminoalkyl group, in combination with specific aminophenol and m-phenylenediamine couplers.

However, these dyes do not satisfy all the above requirements.

The Applicant has now discovered, entirely surprisingly and unexpectedly, that it is possible to obtain dyes, which are capable of producing powerful, particularly chromatic, bright and relatively unselective colorations, which have excellent properties of resistance to the various attacking factors to which keratin fibers may be subjected, by using as oxidation base the diaminopyrazoles of the formula (I) below or physiologically acceptable salts thereof.

One subject of the present invention is thus compounds derived from diaminopyrazole having the following structure (I):

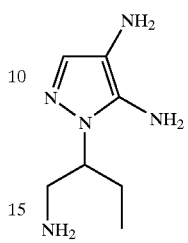

in which $R_1$ is a linear or branched radical chosen from $C_2$, $C_3$ or $C_4$ aminoalkyl or $C_2$, $C_3$ or $C_4$ aminoalkenyl radicals.

The term "$C_2$, $C_3$ or $C_4$ alkyl radical" is understood to mean a hydrocarbonaceous radical with 2, 3 or 4 carbon atoms not comprising unsaturation. In particular, it will relate to ethyl, n-propyl, isopropyl, n-butyl, isobutyl, tert-butyl or 2-methylpropyl radicals.

The term "$C_2$, $C_3$ or $C_4$ alkenyl radical" is understood to mean a hydrocarbonaceous radical with 2, 3 or 4 carbon atoms comprising one or two double bonds.

A subject of the invention is also the physiologically acceptable acid salts of the compounds of formula (I), such as the hydrochlorides, hydrobromides, sulfates, tartrates, lactates or acetates.

A subject of the invention is also a composition for the oxidation dyeing of keratin fibers, and in particular of human keratin fibers such as the hair, characterized in that it contains, in a medium that is suitable for dyeing, as oxidation base, at least one diaminopyrazole of formula (I) above, or physiologically acceptable acid salts thereof.

As mentioned above, the colorations obtained with the oxidation dye composition in accordance with the invention are powerful, particularly bright and chromatic. They in particular produce red shades that are free of or contain very little blue or yellow. Furthermore, they show excellent properties of resistance with respect to the action of various external agents (light, bad weather, washing, permanent-waving, perspiration and friction).

A subject of the invention is also a process for the oxidation dyeing of keratin fibers using such a dye composition.

As examples of diaminopyrazoles of formula (I) according to the invention, mention may be made of the following compounds:

| Structure | Name |
|---|---|
| 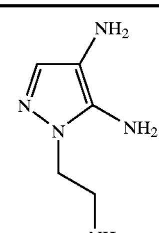 | 2-(2-Amino-ethyl)-2H-pyrazole-3,4-diamine |

-continued

| Structure | Name |
|---|---|
| 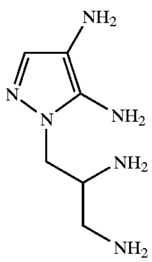 | 2-(2,3-Diamino-propyl)-2H-pyrazole-3,4-diamine |
| 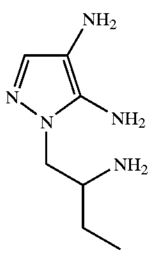 | 2-(2-Amino-butyl)-2H-pyrazole-3,4-diamine |
| 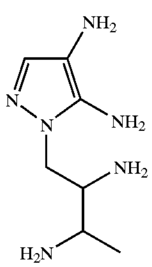 | 2-(2,3-Diamino-butyl)-2H-pyrazole-3,4-diamine |
| 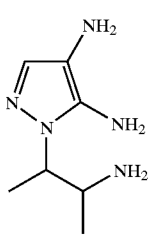 | 2-(2-Amino-1-methyl)-propyl)-2H-pyrazole-3,4-diamine |
| 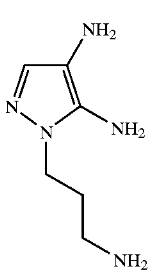 | 2-(3-Amino-propyl)-2H-pyrazole-3,4-diamine |

-continued

| Structure | Name |
|---|---|
| 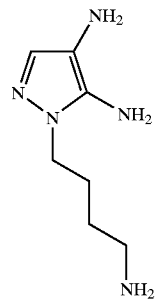 | 2-(4-Amino-butyl)-2H-pyrazole-3,4-diamine |
| 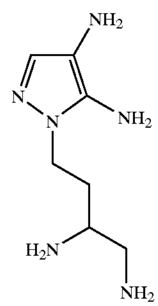 | 2-(3,4-Diamino-butyl)-2H-pyrazole-3,4-diamine |
| 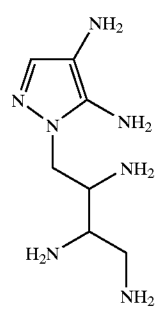 | 4-(4,5-Diamino-pyrazol)-1-yl)-butane-1,2,3-triamine |
| 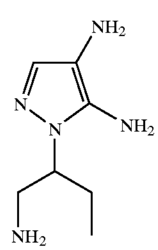 | 2-(1-Aminomethyl-propyl)-2H-pyrazole-3,4-diamine |
| 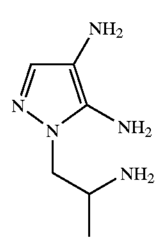 | 2-(2-Amino-propyl)-2H-pyrazole-3,4-diamine |

-continued

| Structure | Name |
|---|---|
| 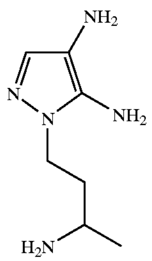 | 2-(3-Amino-butyl)-2H-pyrazole-3,4-diamine |
| 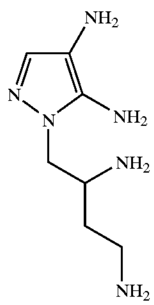 | 2-(2,4-Diamino-butyl)-2H-pyrazole-3,4-diamine |
| 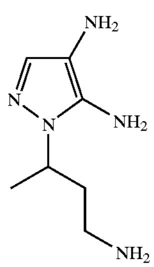 | 2-(3-Amino-1-methyl-propyl)-2H-pyrazole-3,4-diamine |
| 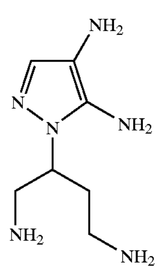 | 2-(3-Amino-1-aminomethl-propyl)-2H-pyrazole-3,4-diamine |
| 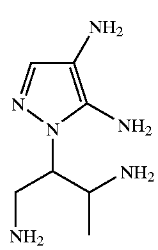 | 2-(2-Amino-1-aminomethyl-propyl)-2H-pyrazole-3,4-diamine |

-continued

| Structure | Name |
|---|---|
| 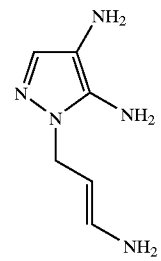 | 2-(3-amino-pro2-ene)-2H-pyrazole-3,4-diamine |
| 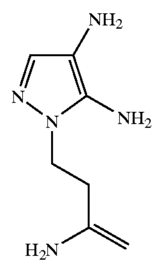 | 2-(3-aminobut-3-ene)-2H-pyrazole-3,4-diamine |
| 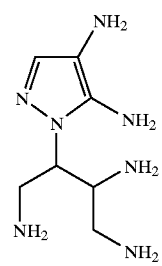 | 2-(2,3-diamino-1-aminomethyl-propyl)-2H-pyrazole-3,4-diamine |
| 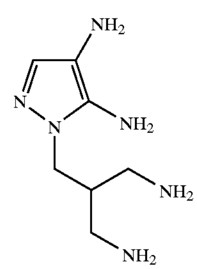 | 2-(3-Amino-2-aminomethyl-propyl)-2H-pyrazole-3,4-diamine |
| 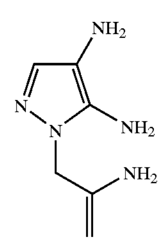 | 2-(2-Amino-prop-2-ene)-2H-pyrazole-3,4-diamine |
| 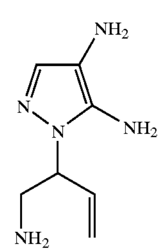 | 2-(1-aminomethyl-prop-2-ene)-2H-pyrazole-3,4-diamine |

| Structure | Name |
|---|---|
| 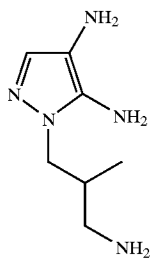 | 2-(3-Amino-2-methyl-propyl)-2H-pyrazole-3,4-diamine |
| 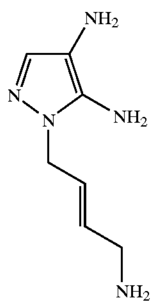 | 2-(4-amino-but-2-ene)-2H-pyrazole-3,4-diamine |

The diaminopyrazoles of formula (I) that are preferred according to the invention have the following structures:

| Structure | Name |
|---|---|
| 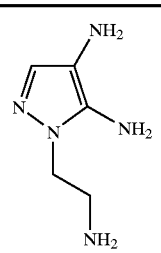 | 2-(2-Amino-ethyl)-2H-pyrazole-3,4-diamine |
| 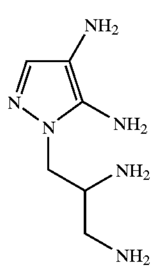 | 2-(2,3-Diamino-propyl)-2H-pyrazole-3,4-diamine |
| 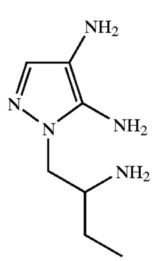 | 2-(2-Amino-butyl)-2H-pyrazole-3,4-diamine |

| Structure | Name |
|---|---|
| 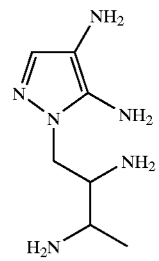 | 2-(2,3-Diamino-butyl)-2H-pyrazole-3,4-diamine |
| 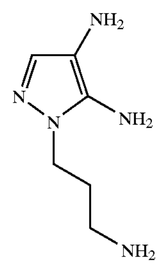 | 2-(3-Amino-propyl)-2H-pyrazole-3,4-diamine |
| 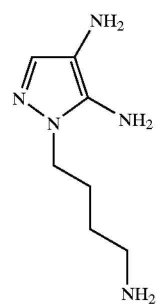 | 2-(4-Amino-butyl)-2H-pyrazole-3,4-diamine |
| 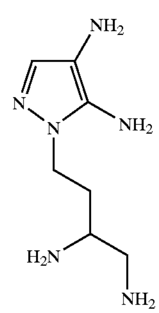 | 2-(3,4-Diamino-butyl)-2H-pyrazole-3,4-diamine |
| 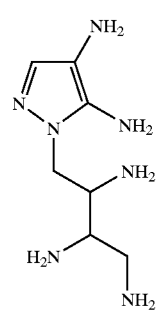 | 4-(4,5-Diamino-pyrazol-1-yl)-butane-1,2,3-triamine |

| Structure | Name |
|---|---|
| 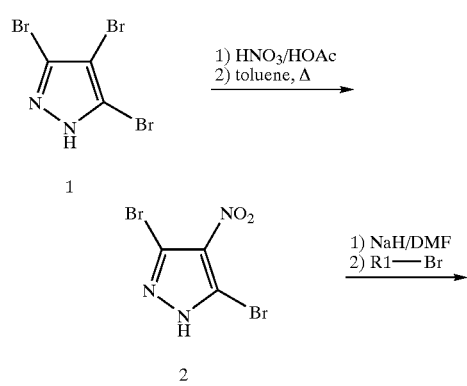 | 2-(2-Amino-propyl)-2H-pyrazole-3,4-diamine |
| 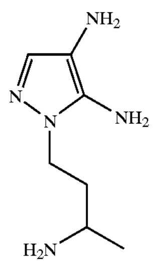 | 2-(3-Amino-butyl)-2H-pyrazole-3,4-diamine |
| 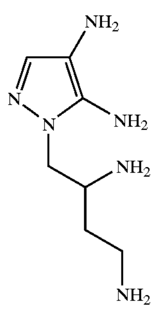 | 2-(2,4-Diamino-butyl)-2H-pyrazole-3,4-diamine |

The diaminopyrazoles of formula (I) that are more particularly preferred according to the invention are 2-(2-aminoethyl)-2H-pyrazole-3,4-diamine, 2-(3-aminopropyl)-2H-pyrazole-3,4-diamine, 2-(2-aminopropyl)-2H-pyrazole-3,4-diamine, 2-(4-aminobutyl)-2H-pyrazole-3,4-diamine and 2-(3-aminobutyl)-2H-pyrazole-3,4-diamine, or the addition salts thereof with physiologically acceptable acids.

The diaminopyrazoles of formula (I) according to the invention are prepared, for example, according to the following general preparation method:

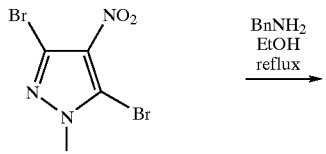

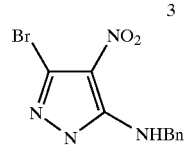

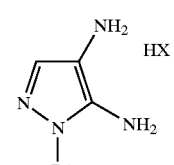

The synthetic approach shown below is described in the literature up to intermediate (2) (J. H. P. Juffermanns, C. L.; Habraken; J. Org. Chem., 1986, 51, 4656; Klebe et al., Synthesis, 1973, 294; R. Hüttel, F. Büchele; Chem. Ber., 1955, 88, 1586).

The alkylation and the amination to obtain the compounds of the type (5) of formula (I) according to the invention are mentioned, for example, in document DE 42 34 885.

The dye composition according to the invention especially contains from 0.001% to 10% by weight, preferably from 0.05% to 6% by weight and even more preferably from 0.1% to 3% by weight of at least one diaminopyrazole of formula (I) or of the salts thereof.

The dye composition in accordance with the invention may also contain, in addition to the diaminopyrazole(s) defined above, at least one additional oxidation base that may be chosen from the oxidation bases conventionally used in oxidation dyeing and among which mention may be made especially of para-phenylenediamines, bis(phenyl)alkylenediamines, para-aminophenols, ortho-aminophenols and heterocyclic bases other than the diaminopyrazoles used in accordance with the invention.

Among the para-phenylenediamines that may be mentioned more particularly, for example, are para-phenylenediamine, para-tolylenediamine, 2,6-dimethyl-para-phenylenediamine, 2-β-hydroxyethyl-para-phenylenediamine, 2-n-propyl-para-phenylenediamine, 2-isopropyl-para-phenylenediamine, N-(β-hydroxypropyl)-para-phenylenediamine, N,N-bis(β-hydroxyethyl)-para-phenylenediamine, 4-amino-N-(β-methoxyethyl)aniline and the para-phenylenediamines described in French patent application FR 2 630 438, and the addition salts thereof.

Among the bis(phenylalkylenediamines that may be mentioned more particularly, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl) ethylenediamine, N,N'-bis(4-aminophenyl) tetramethylenediamine, N,N'-bis(β-hydroxyethyl)-N,N'-bis(4-aminophenyl)tetramethylenediamine, N,N'-bis(4-methylaminophenyl)tetramethylenediamine and N,N'-bis(ethyl)-N,N'-bis(4'-amino-3'-methylphenyl) ethylenediamine, and the addition salts thereof.

Among the para-aminophenols that may be mentioned more particularly, for example, are para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol and 4-amino-2-(β-hydroxyethylaminomethyl)phenol, and the addition salts thereof.

Among the ortho-aminophenols that may be mentioned more particularly, for example, are 2-aminophenol, 2-amino-5-methylphenol, 2-amino-6-methylphenol and 5-acetamido-2-aminophenol, and the addition salts thereof.

Among the heterocyclic bases that may be mentioned more particularly, for example, are pyridine derivatives, pyrimidine derivatives, pyrazole derivatives other than the diaminopyrazoles of formula (I) used in accordance with the invention, and the addition salts thereof.

When they are used, these additional oxidation bases preferably represent from 0.0005% to 12% by weight relative to the total weight of the dye composition and even more preferably from 0.005% to 6% by weight relative this weight.

The oxidation dye compositions in accordance with the invention may also contain at least one coupler and/or at least one direct dye, especially to modify the shades or to enrich them with glints.

The couplers that may be used in the oxidation dye compositions in accordance with the invention may be chosen from the couplers conventionally used in oxidation dyeing, and among which mention may be made especially of meta-phenylenediamines, meta-aminophenols, meta-diphenols, mono- or polyhydroxylated naphthalene derivatives and heterocyclic couplers such as, for example, indole or pyridine derivatives, and the addition salts thereof.

These couplers are chosen more particularly from 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene and 2,6-bis(β-hydroxyethylamino) toluene, and the addition salts thereof.

When they are present, these couplers especially represent from 0.0001% to 10% of the total weight of the dye composition, preferably from 0.005% to 5% by weight and even more preferably from 0.1% to 3% of this weight.

In general, the addition salts with an acid that may be used in the context of the dye compositions of the invention (oxidation bases and couplers) are chosen especially from the hydrochlorides, hydrobromides, sulfates, tartrates, lactates and acetates.

The medium that is suitable for dyeing (or support) used according to the invention consists of water or of a mixture of water and at least one organic solvent chosen from $C_1$–$C_4$ lower alkanols, polyols and polyol ethers, aromatic alcohols, similar products and mixtures thereof.

The dye composition according to the invention may also contain various adjuvants conventionally used in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, mineral or organic thickeners, antioxidants, reducing agents, sunscreens, penetrating agents, sequestering agents, fragrances, buffers, dispersants, conditioners, for instance silicones, film-forming agents, preserving agents and opacifiers.

The pH of the dye composition according to the invention is between 3 and 12.

Needless to say, a person skilled in the art will take care to select this or these optional additional compound(s) such that the advantageous properties intrinsically associated with the oxidation dye composition in accordance with the invention are not, or are not substantially, adversely affected by the envisaged addition(s).

The dye composition according to the invention may be in various forms, such as in the form of liquids, creams or gels, or in any other form that is suitable for dyeing keratin fibers, and especially human hair.

Another subject of the invention is a process for dyeing keratin fibers, and in particular human keratin fibers such as the hair, using the dye composition as defined above.

According to this process, at least one dye composition as defined above is applied to the fibers, for a time that is sufficient to develop the desired coloration, either in air or using an oxidizing agent. The dye composition may optionally contain oxidation catalysts, so as to accelerate the oxidation process.

According to a first embodiment of the process of the invention, the coloration of the fibers may be performed without adding an oxidizing agent, solely by contact with atmospheric oxygen.

According to a second embodiment of the process of the invention, at least one dye composition as defined above is applied to the fibers, the color being revealed at acidic, neutral or alkaline pH using an oxidizing agent that is added to the composition just at the time of use, or which is present in an oxidizing composition applied simultaneously or sequentially in a separate manner.

According to this second embodiment of the dyeing process of the invention, the dye composition described above is preferably mixed, at the time of use, with an oxidizing composition containing, in a medium that is suitable for dyeing, at least one oxidizing agent present in an amount that is sufficient to develop a coloration. The mixture obtained is than applied to the keratin fibers and is left for an action time of 3 to 50 minutes and preferably 5 to 30 minutes, after which the fibers are rinsed, washed with shampoo, rinsed again and dried.

The oxidizing agent present in the oxidizing composition as defined above may be chosen from the oxidizing agents conventionally used for the oxidation dyeing of keratin fibers, and among which mention may be made of hydrogen peroxide, urea peroxide, alkali metal bromates and persalts such as perborates and persulfates. Hydrogen peroxide is particularly preferred.

The pH of the oxidizing composition containing the oxidizing agent as defined above is such that, after mixing with the dye composition, the pH of the resulting composition applied to the keratin fibers preferably ranges between 3 and 12, and even more preferably between 5 and 11. It is adjusted to the desired value by means of acidifying or basifying agents usually used in the dyeing of keratin fibers, and as defined above.

The oxidizing composition as defined above may also contain various adjuvants conventionally used in compositions for dyeing the hair and as defined above.

The composition that is finally applied to the keratin fibers may be in various forms, such as in the form of liquids, creams or gels, or in any other form that is suitable for dyeing keratin fibers, and especially human hair.

Another subject of the invention is a multi-compartment device or dyeing "kit" or any other multi-compartment packaging system, a first compartment of which contains the dye composition as defined above, and a second compartment of which contains the oxidizing composition as defined above. These devices may be equipped with a means for applying the desired mixture to the hair, such as the devices described in patent FR-2 586 913 in the name of the Applicant.

The examples that follow are intended to illustrate the invention without, however, limiting its scope.

EXAMPLES

Synthetic Scheme with
$R_1 = -NH-CO-O-C(CH_3)_3$

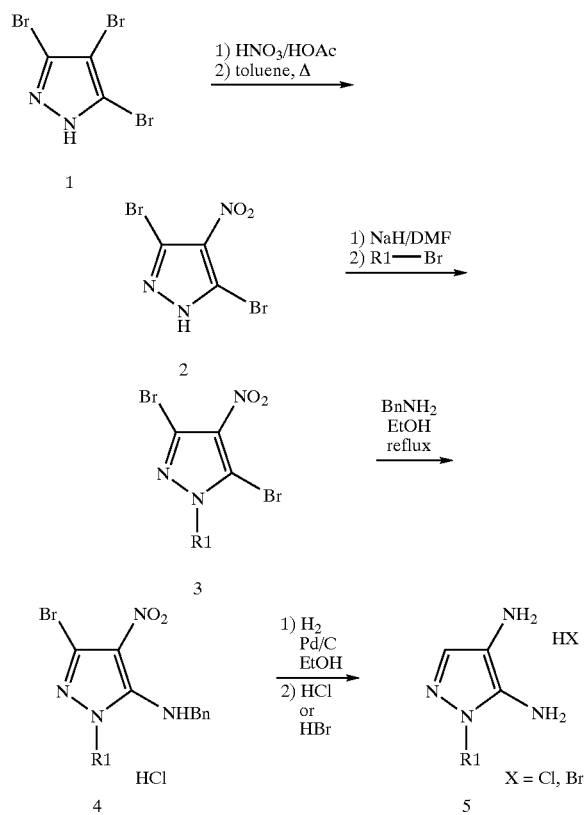

Synthetic Example

Synthesis of
2-(2-aminoethyl)-2H-pyrazole-3,4-diamine
hydrobromide

Synthesis of 3,4,5-tribromopyrazole (1):

An aqueous solution (350 ml) containing sodium hydroxide (24 g, 0.6 mol) and pyrazole (10 g, 0.147 mol) was prepared with stirring (the temperature of the reaction medium rose up to 35° C.). After cooling the reaction medium to 20° C., Br$_2$ (72 g, 0.45 mol) was added dropwise over 1 hour, while maintaining the temperature between 20° C. and 25° C. The reaction was monitored by thin layer chromatography (TLC). The precipitate was filtered off and washed with demineralized water (100 ml). The filtrate was acidified to pH 6–7 using HCl (10%, 33 g, 0.27 mol) and maintaining the temperature between 20 and 25° C. The precipitate thus formed was filtered off and washed with demineralized water (100 ml). The combined solids were maintained at reflux in a Dean-Stark apparatus in the presence of toluene (200 ml). At the end of collection of the water, the organic phase was filtered while hot. The solvent was evaporated down to a residual volume of 110 ml. The solution was cooled to 0–50° C. for 1 hour. The precipitate formed was collected by filtration, washed with cold toluene (20 ml) and dried under vacuum at 80° C. to give the 3,4,5-tribromopyrazole (1) in the form of an off-white solid (30 g, 67%).

$^{13}$C NMR (100 MHz, d$_6$-DMSO): 97.7, 116.1, 126.4
Melting point: 182–184° C.

Synthesis of 3,5-dibromo-4-nitropyrazole (2):

HNO$_3$ (d=1.50 g/ml; 18 ml, 0.429 mol) was added dropwise over 10 minutes to a solution of 3,4,5-tribromopyrazole (1) (50 g, 0.164 mol) in glacial acetic acid (750 ml) while maintaining the temperature at 15° C. Acetic anhydride (250 ml) was added and the reaction mixture was stirred at room temperature for 2 hours. Once the reaction was complete, the reaction mixture was poured onto crushed ice (1 kg). After stirring for 1 hour, the crude product was filtered off and then washed with demineralized water (2×60 ml) to give crude 1-nitro-3,4,5-tribromopyrazole. The water (24.6 ml) contained in the wet product was removed by heating a solution of the product in toluene (750 ml) at reflux in a Dean-Stark apparatus. The toluene solution was maintained at reflux for a further 30 minutes until a TLC (eluent:toluene) showed that the rearrangement of the 1-nitro-3,4,5-tribromopyrazole (Rf=0.77), the intermediate formed, into 3,5-dibromo-4-nitropyrazole (2) (Rf=0.05) was complete. The solution was concentrated to a residual volume of 150 ml and then allowed to cool to 60° C., followed by addition of hexane (275 ml). The solution was cooled to 0–5° C. for 1 hour and the 3,5-dibromo-4-nitropyrazole (2) (29.1 g, 65%) was recovered by filtration and drying under vacuum in the form of a pale yellow solid.

Melting point: 127.6–130.1° C.

Synthesis of [2-(3,5-dibromo-4-nitropyrazol-1-yl)ethyl]carbamic acid tert-butyl ester (3):

A solution of 3,5-dibromo-4-nitropyrazole (2) (16.0 g, 59 mmol) in DMF (130 ml) was added dropwise over 20 min to a stirred solution of NaH (2.6 g, 65 mmol; 60% dispersion in oil washed beforehand with hexane under an inert atmosphere) in DMF (80 ml). After stirring for 10 min, a solution of (2-bromoethyl)carbamic acid tert-butyl ester (19.85 g, 88.5 mmol; obtained by reaction of 2-bromoethylamine with di(tert-butyl)dicarabonate) in DMF (35 ml) was added dropwise over 10 min. The reaction mixture was heated at 80° C. for 3 h and then the DMF was evaporated under reduced pressure. A mixture of DCM/water (200 ml, 1/1) was added to the residue and the organic phase was washed with water (100 ml). The organic phase was dried over Na$_2$SO$_4$ and the solvent was evaporated under reduced pressure. The [2-(3, 5-dibromo-4-nitropyrazol-1-yl)ethyl]carbamic acid tert-butyl ester (3.6 g, 15%) was obtained in the form of a pale yellow solid.

$^1$H NMR (400 MHz, d$_6$-DMSO): 7.02 (1H, t, CH$_2$CH$_2$NH), 4.29 (2H, t, CH$_2$CH$_2$NH), 3.37 (2H, m, CH$_2$CH$_2$NH), 1.35 (9H, s, CH$_3$).

Synthesis of [2-(5-benzylamino-3-bromo-4-nitropyrazol-1-yl)ethyl]carbamic acid tert-butyl ester (4):

A mixture of [2-(3,5-dibromo-4-nitropyrazol-1-yl)ethyl] carbamic acid tert-butyl ester (3.5 g; 8.45 mmol), EtOH (100 ml) and benzylamine (12.9 g, 117 mmol) was heated at reflux for 1.5 h. The reaction medium was concentrated as much as possible under reduced pressure. The residue was taken up in DCM (100 ml) and the organic phase was washed with water (5×50 ml) until all excess benzylamine had been removed and was then dried over $Na_2SO_4$. The organic solvent was evaporated under reduced pressure to give the [2-(5-benzylamino-3-bromo-4-nitropyrazol-1-yl) ethyl]carbamic acid tert-butyl ester (2.5 g, 67%) in the form of a pale yellow solid.

$^1$H NMR (400 MHz, $d_6$-DMSO): 8.00 (1H, t, $NH_{Bn}$) 7.32 (5H, m, $H_{Bn}$), 7.05, (1H, t, $NH_{BOC}$), 4.70 (2H, d, J=8 Hz, $CH_{2Bn}$), 3.94 (2H, m, $CH_2CH_2NH$), 3.22 (2H, m, $CH_2CH_2NH$), 1.35 (9H, s, $CH_3$).

Synthesis of 2-(2-aminoethyl)-2H-pyrazole-3,4-diamine hydrobromide (5):

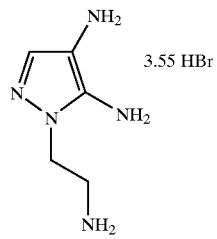

A mixture of [2-(5-benzylamino-3-bromo-4-nitropyrazol-1-yl)ethyl]carbamic acid tert-butyl ester (2.1 g; 4.76 mmol) in EtOH (100 ml) containing a 5% Pd/C catalyst (Engelhard type, 50% moisture, 0.4 g wet weight) was hydrogenated in an autoclave (250 ml) at 15 bar for 3 h. The catalyst was filtered off under an inert atmosphere and washed with EtOH, and the filtrate was recovered in an ethanolic solution (25 ml) containing hydrobromic acid (47%, 2 ml). The orange-colored solution was evaporated to dryness to give the 2-(2-aminoethyl)-2H-pyrazole-3,4-diamine in the hydrobromide form (3.55 HBr) as a pale pink solid (1.5 g, 92%).

Elemental analysis ($C_5H_{11}N_4$, 3.55 HBr; MW=428.41 g/mol) Found: C: 14.82%, H: 3.35%, N: 16.99%, Br: 62.89%. Theory: C: 14.02%. H: 3.42%, N: 16.35%, Br: 66.21%.

$^1$H NMR (400 MHz, $d_6$-DMSO): 9.62 (2H, $S_{broad}$, HBr), 7.98 (2H, $S_{broad}$, $CH_2CH_2NH_2$), 7.37 (1H, s, $H_{pyrazole}$), 6.68 (4H, $S_{broad}$, $NH_2$), 4.17 (2H, t, $CH_2CH_2NH_2$), 3.21 (2H, m, $CH_2CH_2NH_2$).

Examples of Dye Composition in Alkaline Medium

The following composition is prepared:

| | |
|---|---|
| diaminopyrazole base of formula (I) | 5 × 10$^{-3}$ mol |
| coupler | 5 × 10$^{-3}$ mol |
| oleyl alcohol polyglycerolated with 2 mol of glycerol | 4.0 g |
| oleyl alcohol polyglycerolated with 4 mol of glycerol, containing 78% active material (A.M.) | 5.7 g A.M. |
| oleic acid | 3.0 g |
| oleylamine containing 2 mol of ethylene oxide, sold under the trade name Ethomeen O12 by the company Akzo | |
| diethylaminopropyl laurylamino succinamate, sodium salt, at 55% A.M. | 3.0 g A.M. |
| oleyl alcohol | 5.0 g |
| oleic acid diethanolamide | 12.0 g |
| propylene glycol | 3.5 g |
| ethyl alcohol | 7.0 g |
| dipropylene glycol | 0.5 g |
| propylene glycol monomethyl ether | 9.0 g |
| sodium metabisulfite as an aqueous solution containing 35% A.M. | 0.455 g A.M. |
| ammonium acetate | 0.8 g |
| antioxidant, sequestering agent | qs |
| fragrance, preserving agent | qs |
| aqueous ammonia containing 20% $NH_3$ | 100 g | pH = 9.5
A.M. means "active material"

The base and the coupler are as defined below.

| DYEINGS AT ALKALINE pH | | |
|---|---|---|
| Examples | Base | Coupler |
| 1 | 2-(2-aminoethyl)-2H-pyrazole-3,4-diamine | m-aminophenol |
| 2 | 2-(2-aminoethyl)-2H-pyrazole-3,4-diamine | 6-chloro-2-methyl-5-aminophenol |
| 3 | 2-(2-aminoethyl)-2H-pyrazole-3,4-diamine | 2,4-diamino-1(β-hydroxyethyloxy)-benzene dihydrochloride |
| 4 | 2-(2-aminoethyl)-2H-pyrazole-3,4-diamine | 2-methyl-5-aminophenol |

At the time of use, each dye composition is mixed, weight for weight, with a 20-volumes aqueous hydrogen peroxide solution (6% by weight), the pH of which has been adjusted to about 2.5 with orthophosphoric acid.

The mixture is applied to natural gray hair containing 90% white hairs, at a rate of 5 g per 0.5 g of hair.

After 30 minutes, the hair is then rinsed, washed with a standard shampoo, rinsed again and dried.

The color of the locks was evaluated in the L*a*b* system, on white hair, using a Minolta CM 2002 spectrophotometer.

In the L*a*b* space, the lightness is indicated by the value L* on a scale from 0 to 100, while the chromatic data is expressed by a* and b* which indicate two color axes, a* the red-green axis and b* the yellow-blue axis.

According to this system, the higher the value of L, the paler and less intense the color. Conversely, the lower the value of L, the darker or more intense the color.

| | White hair | | |
|---|---|---|---|
| Examples | L* | a* | b* |
| Example 1 | 35.1 | 27.5 | 13.9 |
| Example 2 | 41.9 | 25.0 | 15.2 |
| Example 3 | 30.7 | 21.3 | 2.1 |
| Example 4 | 41.8 | 27.1 | 24.5 |

The diaminopyrazoles according to the invention thus make it possible to obtain strong and chromatic shades at alkaline pH.

Example of Dye Composition in Neutral Medium

The same formulations as above are prepared, replacing the aqueous ammonia with citric acid in an amount such that the pH is equal to 7.

| | DYEING AT NEUTRAL pH | |
|---|---|---|
| Example | Base | Coupler |
| 5 | 2-(2-aminoethyl)-2H-pyrazole-3,4-diamine | 2-methyl-5-aminophenol |

Locks of natural and permanent-waved gray hair containing 90% white hairs are dyed with the dye composition 5 and 6 above in the same manner as for the dyeing at alkaline pH.

The following shades are obtained:

| | Natural white hair | | |
|---|---|---|---|
| Example | L* | a* | b* |
| Example 5 | 41.6 | 17.8 | 17.8 |

At neutral pH, the diaminopyrazoles according to the invention make it possible to obtain strong shades.

The invention claimed is:

1. A diaminopyrazole compound of formula (I):

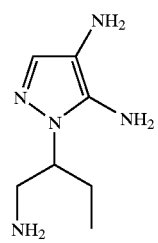

in which $R_1$ is a linear or branched radical further defined as a $C_2$, $C_3$ or $C_4$ aminoalkyl or $C_2$, $C_3$ or $C_4$ aminoalkenyl radicals, and wherein the compound of formula (I) is further defined as 2-(2-aminoethyl)-2-H-pyrazole-3,4-diamine, 2-(3-aminopropyl)-2H-pyrazole-3,4-diamine, 2-(2-aminopropyl)-2H-pyrazole-3,4-diamine, 2-(2,3-diamino-propyl)-2H-pyrazole-3,4-diamine, 2-(4-aminobutyl)-2H-pyrazole-3,4-diamine, 2-(3-aminobutyl)-2H-pyrazole-3,4-diamine, 2-(2-aminobutyl)-2H-pyrazole-3,4-diamine, 2-(3,4-diaminobutyl)-2H-pyrazole-3,4-diamine, 2-(2,4-diaminobutyl)-2H-pyrazole-3,4-diamine, 2-(2,3-diaminobutyl)-2H-pyrazole-3,4-diamine, 4-(4,5-diaminopyrazol-1-yl)-butane-1,2,3-triamine, 2-(3-amino-1-methylpropyl)-2H-pyrazole-3,4-diamine, 2-(2-amino-1-methyl-propyl)-2H-pyrazole-3,4-diamine, 2-(1-aminomethylpropyl)-2H-pyrazole-3,4-diamine, 2-(3-amino-1-amino-methylpropyl)-2H-pyrazole-3,4-diamine, 2-(2-amino-1-aminomethylpropyl)-2H-pyrazole-3,4-diamine, 2-(2,3-diamino-1-aminomethylpropyl)-2H-pyrazole-3,4-diamine, 2-(3-amino-2-methylpropyl)-2H-pyrazole-3,4-diamine, 2-(3-amino-2-aminomethylpropyl)-2H-pyrazole-3,4-diamine, 2-(3-aminoprop-2-ene)-2H-pyrazole-3,4-diamine, 2-(2-aminoprop-2-ene)-2H-pyrazole-3,4-diamine, 2-(4-aminobut-2-ene)-2H-pyrazole-3,4-diamine, 2-(3-aminobut-3-ene)-2H-pyrazole-3,4-diamine, 2-(1-aminomethylprop-2-ene)-2H-pyrazole-3,4-diamine, or a physiologically acceptable acid salt of any of these.

2. The compound of claim 1, wherein the physiologically acceptable salt is a hydrochloride, hydrobromide, sulfate, tartrate, lactate, or acetate.

3. A composition for the oxidation dyeing of keratin fibers, comprising, as an oxidation base, a diaminopyrazole compound of formula (I):

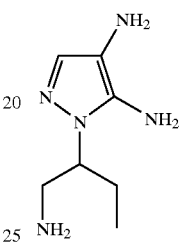

in which $R_1$ is a linear or branched radical further defined as a $C_2$, $C_3$ or $C_4$ aminoalkyl or $C_2$, $C_3$ or $C_4$ aminoalkenyl radicals, or a physiologically acceptable salt thereof, in a medium suitable for dying.

4. The composition of claim 3, further defined as comprising from 0.001% to 10% by weight of at least one diaminopyrazole of formula (I) or salt thereof.

5. The composition of claim 3, wherein the medium that is suitable for dyeing comprises water or a mixture of water and at least one organic solvent further defined as a $C_1$–$C_4$ lower alkanol, polyol, polyol ether, or aromatic alcohol, or a mixture thereof.

6. The composition of claim 3, further defined as having a pH of between 3 and 12.

7. The composition of claim 3, comprising at least one additional oxidation base further defined as a para-phenylenediamine, bis(phenyl)alkylenediamine, para-aminophenol, ortho-aminophenol, or heterocyclic base other than the diaminopyrazole of formula (I), or an addition salt of one of these with an acid.

8. The composition of claim 7, wherein the additional oxidation base comprises from 0.0005% to 12% by weight relative to the total weight of the dye composition.

9. The composition of claim 3, further defined as comprising at least one direct dye.

10. The composition of claim 3, further defined as comprising at least one coupler.

11. The composition of claim 10, wherein the coupler is a meta-phenylenediamine, meta-aminophenol, meta-diphenol, monohydroxylated naphthalene derivative, polyhydroxylated naphthalene derivative, or heterocyclic coupler, or an addition salt of one of these with an acid.

12. The composition of claim 10, wherein the coupler represents from 0.0001% to 10% by weight relative to the total weight of the dye composition.

13. The composition of claim 3, further defined as comprising at least one direct dye and at least one coupler.

14. A process for dyeing keratin fibers, comprising applying to the fibers a composition comprising, as an oxidation base, a diaminopyrazole compound of formula (I):

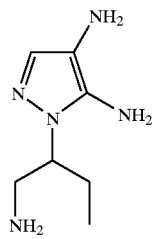

in which $R_1$ is a linear or branched radical further defined as a $C_2$, $C_3$ or $C_4$ aminoalkyl or $C_2$, $C_3$ or $C_4$ aminoalkenyl radicals, or a physiologically acceptable salt thereof, in a medium suitable for dying, for a time that is sufficient to develop the desired coloration, either in air or using an oxidizing agent.

15. The process of claim 14, wherein the keratin fibers are further defined as human hair.

16. The process of claim 14, further comprising applying to the fibers an oxidation catalyst.

17. The process of claim 14, wherein no oxidizing agent is applied and coloration is revealed by contact with atmospheric oxygen.

18. The process of claim 14, further comprising an application of an oxidizing agent to the fibers.

19. The process of claim 18, wherein the oxidizing agent is added to the dye composition prior to application of the dye composition to the fibers.

20. The process of claim 18, wherein the oxidizing agent is comprised in an oxidizing composition that is applied simultaneously or sequentially with regard to the dyeing composition to the fibers.

21. The process of claim 18, wherein the oxidizing agent is hydrogen peroxide, urea peroxide, an alkali metal bromate, or a persalt.

22. A kit comprising:
a first compartment containing a composition comprising a diaminopyrazole compound of formula (I):

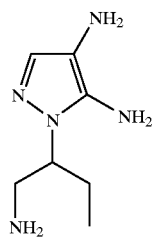

in which $R_1$ is a linear or branched radical further defined as a $C_2$, $C_3$ or $C_4$ aminoalkyl or $C_2$, $C_3$ or $C_4$ aminoalkenyl radicals, or a physiologically acceptable salt thereof, in a medium suitable for dying; and a second compartment containing an oxidizing composition.

23. A composition for oxidation dyeing of keratin fibers comprising, as an oxidation base, from 0.001% to 10% by weight of at least one diaminopyrazole of formula (I):

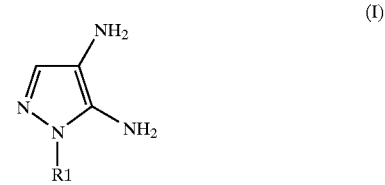

in which $R_1$ is a linear or branched radical further defined as a $C_2$, $C_3$ or $C_4$ aminoalkyl or $C_2$, $C_3$ or $C_4$ aminoalkenyl radicals, or a physiologically acceptable salt thereof, in a medium suitable for dying.

24. A process for dyeing human hair, comprising applying to the hair a composition comprising, as an oxidation base, a diaminopyrazole compound of formula (I):

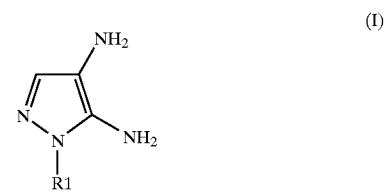

in which $R_1$ is a linear or branched radical further defined as a $C_2$, $C_3$ or $C_4$ aminoalkyl or $C_2$, $C_3$ or $C_4$ aminoalkenyl radicals, or a physiologically acceptable salt thereof, in a medium suitable for dying, for a time that is sufficient to develop the desired coloration, either in air or using an oxidizing agent.

* * * * *

UNITED STATES PATENT AND TRADEMARK OFFICE
CERTIFICATE OF CORRECTION

PATENT NO. : 7,014,663 B2  Page 1 of 1
APPLICATION NO. : 10/484131
DATED : March 21, 2006
INVENTOR(S) : Thilo Fessmann and Eric Terranova It is certified that error appears in the above-identified patent and that said Letters Patent is hereby corrected as shown below:

(57) Abstract, delete the Abstract and insert the following therefor:

--The invention concerns compounds derived from diaminopyrazole of formula (I), wherein: $R_1$ is a linear or branched radical selected among $C_2$, $C_3$, and $C_4$ aminoalkyl radicals or $C_2$, $C_3$, and $C_4$ aminoalkenyl radicals, or one of the physiologically acceptable salts thereof. The invention also concerns compositions containing said compounds for dyeing keratinous fibers and the of method using said compositions.--

Claim 3, col. 18, ln. 31, delete "dying" and insert --dyeing-- therefor.

Claim 14, col. 19, ln. 19, delete "dying" and insert --dyeing-- therefor.

Claim 22, col. 20, ln. 4, delete "dying" and insert --dyeing-- therefor.

Claim 23, col. 20, ln. 27, delete "dying" and insert --dyeing-- therefor.

Claim 24, col. 20, ln. 49, delete "dying" and insert --dyeing-- therefor.

Signed and Sealed this

First Day of August, 2006

JON W. DUDAS
*Director of the United States Patent and Trademark Office*